(12) United States Patent
Abbaszadeh (10) Patent No.: US 11,337,465 B2
(45) Date of Patent: *May 24, 2022

(54) PUMPING/NURSING BRA

(71) Applicant: Simple Wishes LLC, Dallas, TX (US)

(72) Inventor: Debra Abbaszadeh, San Francisco, CA (US)

(73) Assignee: Simple Wishes LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/550,902

(22) Filed: Aug. 26, 2019

(65) Prior Publication Data

US 2020/0154792 A1 May 21, 2020

Related U.S. Application Data

(63) Continuation of application No. 15/357,596, filed on Nov. 21, 2016, now Pat. No. 10,420,377, which is a (Continued)

(51) Int. Cl.
*A41C 3/04* (2006.01)
*A61M 1/06* (2006.01)

(52) U.S. Cl.
CPC .............. *A41C 3/04* (2013.01); *A61M 1/06* (2013.01); *A61M 1/062* (2014.02); *A61M 2209/088* (2013.01)

(58) Field of Classification Search
CPC ......... A41C 3/04; A41C 3/007; A41C 3/0028; A41C 3/0035; A41C 3/12
(Continued)

(56) References Cited

U.S. PATENT DOCUMENTS

| 623,413 A | 4/1899 | Murray |
| 949,414 A | 2/1910 | Cunningham |

(Continued)

FOREIGN PATENT DOCUMENTS

| AU | 2011100651 A4 | 7/2011 |
| AU | 2013203882 | 10/2014 |

(Continued)

OTHER PUBLICATIONS

Office Action for U.S. Appl. No. 15/357,596, dated Dec. 31, 2018, 12 pages.

(Continued)

*Primary Examiner* — Gloria M Hale (57) ABSTRACT

An apparatus allowing a woman to pump milk from her breasts without the necessity of the woman's hands holding the breast pumps utilizes at least one band of material encircling the woman's chest, the band of material provided with two openings corresponding to the woman's breasts. A center panel would be provided to adjust the fit of the band. Additionally, in another embodiment, a back panel would be used in conjunction with the center panel to connect left and right panels together, the left and right panels including openings for a woman's breast. In all of the embodiments, semicircular pieces would cover each of the openings. In yet another embodiment, a removable piece is attached to the front of the apparatus, allowing the woman to wear the apparatus all day, even in public.

18 Claims, 11 Drawing Sheets

Related U.S. Application Data continuation of application No. 14/867,979, filed on Sep. 28, 2015, now Pat. No. 9,498,005, which is a continuation of application No. 13/692,204, filed on Dec. 3, 2012, now Pat. No. 9,167,855, which is a continuation of application No. 12/585,829, filed on Sep. 25, 2009, now Pat. No. 8,323,070.

(60) Provisional application No. 61/193,731, filed on Dec. 19, 2008.

(58) Field of Classification Search
USPC .......................................................... 450/36
See application file for complete search history.

(56) References Cited

U.S. PATENT DOCUMENTS

| | | |
|---|---|---|
| 2,305,051 A | 11/1940 | Witkower |
| 2,436,430 A | 2/1948 | Hart |
| 2,492,862 A | 12/1949 | Harvey |
| 2,522,010 A | 9/1950 | Woodruff |
| 2,585,338 A | 2/1952 | Meares |
| 2,613,355 A | 10/1952 | Coleman |
| 2,679,048 A | 5/1954 | Alberts |
| 2,738,509 A | 3/1956 | Bauder |
| 3,002,515 A | 10/1961 | Glogover |
| 4,335,728 A | 6/1982 | Fildan |
| 4,640,287 A | 2/1987 | Anderson et al. |
| 4,648,404 A | 3/1987 | Clark |
| 4,878,879 A | 11/1989 | Kunstadter |
| 4,911,677 A | 3/1990 | White |
| 5,098,330 A | 3/1992 | Greenberg |
| 5,334,082 A | 8/1994 | Barker |
| 5,341,514 A | 8/1994 | Dale |
| 5,380,238 A | 1/1995 | Crew-Gee |
| 5,395,280 A | 3/1995 | Greenberg |
| 5,514,166 A | 5/1996 | Silver et al. |
| 5,575,768 A | 11/1996 | Lockridge et al. |
| 5,616,125 A | 4/1997 | Jelks |
| 5,624,296 A | 4/1997 | Weber-Unger |
| 5,690,537 A | 11/1997 | Kalmus |
| 6,004,186 A | 12/1999 | Penny |
| 6,027,396 A | 2/2000 | Yonchar |
| 6,086,451 A | 7/2000 | Fernandes |
| 6,227,936 B1 | 5/2001 | Mendoza |
| 6,247,996 B1 | 6/2001 | Fields |
| 6,319,092 B1 | 11/2001 | Leyhe et al. |
| 6,438,758 B1 | 8/2002 | Burkard et al. |
| 6,440,100 B1 | 8/2002 | Prentiss |
| 6,705,920 B1 | 3/2004 | Engel |
| 6,854,132 B1 | 2/2005 | Polzin |
| 6,866,558 B2 | 3/2005 | Luciano et al. |
| 6,887,217 B1 | 5/2005 | Logan |
| 6,974,361 B2 | 12/2005 | Cravaack et al. |
| 7,232,359 B1 | 6/2007 | Richardson |
| 7,306,505 B2 | 12/2007 | Barbour et al. |
| 7,507,141 B2 | 3/2009 | Ward et al. |
| 7,591,706 B2 | 9/2009 | Barbour et al. |
| 8,192,247 B2 | 6/2012 | Abbaszadeh |
| 8,323,070 B2 | 12/2012 | Abbaszadeh |
| 8,523,629 B2 | 9/2013 | Pundyk |
| 9,167,855 B2 | 10/2015 | Abbaszadeh |
| 9,498,005 B2 | 11/2016 | Abbaszadeh |
| 9,872,524 B2 | 1/2018 | Abbaszadeh |
| 9,894,942 B2 | 2/2018 | Burrell |
| 10,212,972 B2 | 2/2019 | Abbaszadeh |
| 10,420,377 B2 * | 9/2019 | Abbaszadeh .......... A61M 1/062 |
| 10,420,378 B2 * | 9/2019 | Kosak ...................... A41C 3/04 |
| 10,426,203 B2 * | 10/2019 | Kosak ...................... A41C 3/04 |
| 10,772,361 B2 | 9/2020 | Abbaszadeh |
| 10,905,173 B1 | 2/2021 | Kosak et al. |
| 2002/0062512 A1 | 5/2002 | Gustafson et al. |
| 2003/0027491 A1 | 2/2003 | Cravaack et al. |
| 2003/0167037 A1 | 9/2003 | Fialkoff |
| 2003/0191433 A1 | 10/2003 | Prentiss |
| 2003/0232573 A1 | 12/2003 | Plew |
| 2004/0016039 A1 | 1/2004 | Caprio |
| 2006/0025039 A1 | 2/2006 | Barbour et al. |
| 2006/0211336 A1 | 9/2006 | Brigham |
| 2007/0161330 A1 | 7/2007 | Whitehead et al. |
| 2008/0022434 A1 | 1/2008 | Adelman |
| 2008/0039781 A1 | 2/2008 | Bjorge |
| 2008/0146118 A1 | 6/2008 | Solberg et al. |
| 2008/0262420 A1 | 10/2008 | Dao et al. |
| 2009/0286452 A1 | 11/2009 | Grayson |
| 2010/0031418 A1 | 2/2010 | Op't Hof |
| 2010/0068971 A1 | 3/2010 | Henderickson |
| 2010/0159801 A1 | 6/2010 | Abbaszadeh |
| 2010/0159802 A1 | 6/2010 | Abbaszadeh |
| 2010/0261410 A1 | 10/2010 | Hirtz |
| 2011/0081826 A1 | 4/2011 | Henderickson |
| 2011/0092134 A1 | 4/2011 | Alva |
| 2011/0237156 A1 | 9/2011 | Boonen et al. |
| 2011/0314587 A1 | 12/2011 | Ritchie |
| 2012/0129427 A1 | 5/2012 | Perez |
| 2012/0184179 A1 | 7/2012 | Blitz |
| 2013/0095727 A1 | 4/2013 | Abbaszadeh |
| 2014/0087625 A1 | 3/2014 | Ironi |
| 2014/0220860 A1 | 8/2014 | Alva |
| 2014/0273737 A1 | 9/2014 | Cortese et al. |
| 2014/0364035 A1 | 12/2014 | Abbaszadeh |
| 2014/0364036 A1 | 12/2014 | Abbaszadeh |
| 2016/0015092 A1 | 1/2016 | Abbaszadeh |
| 2016/0095967 A1 | 4/2016 | Weston |
| 2016/0150834 A1 | 6/2016 | Boele et al. |
| 2017/0172502 A1 | 6/2017 | Rofe et al. |
| 2017/0265530 A1 | 9/2017 | Donlon et al. |
| 2017/0280786 A1 | 10/2017 | Abbaszadeh |
| 2017/0280787 A1 | 10/2017 | Burrell |
| 2018/0064177 A1 | 3/2018 | Akerson et al. |
| 2018/0064178 A1 | 3/2018 | Akerson et al. |
| 2018/0132542 A1 | 5/2018 | Abbaszadeh |
| 2018/0206559 A1 | 7/2018 | Kosak |
| 2018/0255840 A1 | 9/2018 | Abbaszadeh |
| 2018/0352884 A1 | 12/2018 | Vanos |
| 2019/0014829 A1 | 1/2019 | Kim et al. |
| 2019/0142078 A1 | 5/2019 | Kosak |
| 2019/0208839 A1 | 7/2019 | Amos |
| 2019/0261698 A1 | 8/2019 | Akerson et al. |
| 2019/0289926 A1 | 9/2019 | Abbaszadeh |
| 2020/0154793 A1 | 5/2020 | Kosak |
| 2020/0404984 A1 | 12/2020 | Abbaszadeh |

FOREIGN PATENT DOCUMENTS

| | | |
|---|---|---|
| CN | 201479956 U | 5/2010 |
| CN | 104223390 A | 12/2014 |
| CN | 204907978 U | 12/2015 |
| EP | 2810573 | 8/2016 |
| FR | 881406 A | 4/1943 |
| FR | 919893 A | 3/1947 |
| GB | 2536541 A | 9/2016 |
| KR | 2011-0001216 | 2/2011 |
| WO | WO 2007/053073 | 5/2007 |
| WO | WO 2008/005713 | 1/2008 |
| WO | WO 2010/080122 | 7/2010 |
| WO | WO 2011/135092 | 11/2011 |

OTHER PUBLICATIONS

Extended European Search Report for European Application No. 14171556.5, dated Sep. 10, 2014, 5 pages.

Decision on Rejection for Chinese Application No. 201410077245.4, dated Aug. 5, 2019, 26 pages.

Office Action for U.S. Appl. No. 15/872,360, dated Dec. 30, 2019, 14 pages.

Office Action for U.S. Appl. No. 12/453,073, dated Sep. 23, 2011, 11 pages.

International Search Report and Written Opinion for International Application No. PCT/US2009/006618, dated Mar. 8, 2010, 9 pages.

Office Action for U.S. Appl. No. 12/585,829, dated Aug. 24, 2011, 10 pages.

(56) References Cited

OTHER PUBLICATIONS

Office Action for U.S. Appl. No. 13/692,204, dated Oct. 1, 2014, 9 pages.
Office Action for U.S. Appl. No. 13/692,204, dated Jul. 3, 2013, 6 pages.
Office Action for U.S. Appl. No. 13/692,204, dated Apr. 8, 2014, 6 pages.
Office Action for U.S. Appl. No. 14/867,979, dated Nov. 5, 2015, 8 pages.
Office Action for U.S. Appl. No. 14/867,979, dated Apr. 4, 2016, 6 pages.
Extended European Search Report for European Application No. 14171552.4, dated Sep. 9, 2014, 6 pages.
Office Action for European Application No. 14171552.4, dated Dec. 3, 2015, 4 pages.
Office Action for U.S. Appl. No. 14/172,812, dated Jun. 16, 2016, 7 pages.
First Office Action for Chinese Application No. 201410077245.4, dated Dec. 7, 2016, 31 pages.
Second Office Action for Chinese Application No. 201410077245.4, dated Oct. 30, 2017, 29 pages.
Third Office Action for Chinese Application No. 201410077245.4, dated Jul. 9, 2018, 34 pages.
Fourth Office Action for Chinese Application No. 201410077245.4, dated Mar. 21, 2019, 27 pages.
Office Action for U.S. Appl. No. 14/172,826, dated May 20, 2016, 8 pages.
Office Action for U.S. Appl. No. 14/172,826, dated Dec. 29, 2016, 5 pages.
Office Action for U.S. Appl. No. 14/172,826, dated Apr. 10, 2017, 15 pages.
Extended European Search Report for European Application No. 16179769.1, dated Feb. 10, 2017, 8 pages.
Office Action for U.S. Appl. No. 15/873,317, dated Jun. 29, 2018, 9 pages.
International Search Report and Written Opinion for International Application No. PCT/US2016/043326, dated Nov. 28, 2016, 19 pages.
First Office Action for Chinese Application No. 201880007431.7, dated Jul. 3, 2020, 29 pages.
Office Action for European Application No. 18713053.9, dated Oct. 26, 2020, 4 pages.
Office Action for U.S. Appl. No. 15/873,456, dated Mar. 21, 2019, 14 pages.
International Search Report and Written Opinion for International Application No. PCT/US2018/014245, dated Jun. 12, 2018, 15 pages.
Office Action for U.S. Appl. No. 16/201,718, dated Mar. 21, 2019, 11 pages.
Third Party Submission for U.S. Appl. No. 16/551,295, dated Sep. 17, 2020, 23 pages.
Screen captures from YouTube video clip entitled "EverBeautyBra™ by LactaMed™," uploaded Apr. 23, 2018 by user "LactaMed Inc". Retrieved from the Internet: <URL: https://www.youtube.com/watch?v=-KUuqkxejlM>, 2 pages.
LactaMed, "EverBeautyBra™ Hands Free Pumping and Nursing Bra In One," 2020, [Online], Retrieved from the Internet: URL: <https://lactamed.com/products/everbeautybra-all-in-one?_pos=5&_sid=3f52c4eee&_ss=r>, 8 pages.
Office Action for U.S. Appl. No. 16/551,295, dated Oct. 7, 2020, 12 pages.
Nursing Bra Express, "Pump Up the Band Hands Free Nursing Bra," [online], [Retrieved on Mar. 2, 2013], Retrieved from the Internet: URL: <http://www.nursingbraexpress.com/nursing-bras/pump-band-hands-free-nursing-bra>, 1 page.

* cited by examiner

PUMPING/NURSING BRA

CROSS-REFERENCE TO RELATED APPLICATION

The present application is a continuation of U.S. patent application Ser. No. 15/357,596, filed Nov. 21, 2016, now U.S. Pat. No. 10,420,377, which is a continuation of U.S. patent application Ser. No. 14/867,979, filed Sep. 28, 2015, now U.S. Pat. No. 9,498,005, which is a continuation of U.S. patent application Ser. No. 13/692,204, filed Dec. 3, 2012, now U.S. Pat. No. 9,167,855, which is a continuation of U.S. patent application Ser. No. 12/585,829, filed of Sep. 25, 2009, now U.S. Pat. No. 8,323,070, which claims the benefit of U.S. Patent Application Ser. No. 61/193,731, filed Dec. 19, 2008, each of the disclosures of which is hereby incorporated by reference in its entirety.

This application is related to U.S. patent application Ser. No. 16/201,718, filed Nov. 27, 2018, now U.S. Pat. No. 10,420,378, which is a continuation U.S. patent application Ser. No. 15/873,456, filed Jan. 17, 2018, now U.S. Pat. No. 10,426,203, which claims priority to U.S. Provisional Application No. 62/548,706, filed on Aug. 22, 2017, and claims priority to U.S. Provisional Application No. 62/448,622, filed on Jan. 20, 2017.

FIELD OF THE INVENTION

The present invention is directed to a device to assist a woman in pumping breast milk.

BACKGROUND OF THE INVENTION

When using a breast pump, the mother must manually hold the breast flange or shield over the exposed portion of the breast. Due to the length of time required to express milk when using a pump, a woman will often express milk from both breasts simultaneously. To express milk from both breasts, the woman must hold the breast flange or shield with each hand against her breast, leaving her in an awkward position, making it difficult to do something as simple as operating the breast pump. As a result, the nursing mother will not have the full use of both hands to perform other tasks. It would be advantageous to develop a device that would enable a mother to use a breast pump while allowing her the free use of her hands to perform other tasks.

Hands-free pumping affords a mother the ability to simultaneously massage her breasts to enhance milk let down, a procedure that is not possible with most breast pumps currently in use, or to simply engage in other pursuits when the milk is being pumped. To mitigate the disadvantage of holding the storage container while pumping, several inventions have been patented.

U.S. Pat. No. 6,004,186, to Penny, describes an apparatus for securing suction devices to a nursing mother's breast. This apparatus includes a single, elongated chest piece 12 which may be manufactured as a single strip of fabric having an essentially constant width along the entire chest piece. The chest piece 12 may be manufactured of a stretchable, non-woven material or a non-stretchable woven material. FIG. 1 illustrates the apparatus configured as a halter top provided with a seam 18 in the rear of the apparatus. FIG. 2 illustrates the apparatus as a bandeau or tube top having a first end 113*a* and a second end 113*b* of a chest piece 112 which may overlap to temporarily secure the chest piece 112 around the mother's chest. In both of the embodiments, the front portion of the chest piece is provided with two openings allowing a breast pump to be attached to one of the woman's breasts which would fit within a portion 12*c* of the chest piece. The elongated chest piece is arranged to fit snugly around the women's chest and breast without providing support for the nursing woman's breast.

U.S. Pat. No. 6,974,361, to Cravaack et al, discloses a milk extraction device comprising an elastic band having slits aligned with the nipples of the breasts. The band is worn under and is snap attached to a nursing bra, as shown in FIGS. 9-12. The bra is unsnapped to provide a pumping position, as described in column 5, lines 14-16.

U.S. Pat. No. 6,866,558 to Luciano et al, discloses a pumping band having slits aligned with the nipples of the breasts.

U.S. Patent Application Publication 2008/0039781 to Bjorge, illustrates a hands-free breast pump support device 10 that connects to a nursing bra, which can be made from lycra. The device must be worn beneath and attached via connections 110A, 110B, to the nursing bra, as described in paragraph [0018].

U.S. Patent Application Publication 2008/0262420 to Dao et al, discusses a hands-free pumping device that fits into a nursing bra 32.

U.S. Patent Application Publication 2003/0191433 to Prentiss, as well as U.S. Pat. No. 6,440,100, also to Prentiss, discloses a hands-free pumping device that is placed beneath a support bra.

U.S. Pat. No. 6,705,920 to Engel, discloses a breast pump holding a strap that includes elastic bands 18, 20 and slits 34, 36, for placement of the narrow portion 38 of the breast pump cone 12.

U.S. Pat. No. 6,227,936, issued to Mendoza, describes a hand free pumping and nursing bra having a detachable nursing cup and pumping panel.

However, none of these prior art references address the combination of features disclosed in the present invention.

SUMMARY OF THE INVENTION

The present invention is directed to a stylish bustier creating a tight seal between the woman's breasts and the flange shield of the breast pump. The bustier is provided with two side panel portions, each having top and bottom elastic edges to prevent the bustier from slipping down, as well as supporting the woman's breasts. An adjustable strap is attached to both sides of the bustier. In one embodiment, the strap is hooked to the top front edges of both side panel portions and extends around the back of the neck of the woman for added security. Other embodiments would utilize two straps, each strap attached to the front and rear portions of one of the side portions. Each side panel portion is provided with holes corresponding to each of the woman's breasts that would easily allow a woman to insert and remove the flange shield before and after pumping. Each of these holes could be surrounded by an elastic piece, and is provided with four circular pieces as will be subsequently explained.

Since there is a considerable range of sizes and shapes of a woman's breasts, as well as the distance between the apex or nipple, the present invention allows the woman to adjust the front of each of the side panels so that each hole will be centered above the respective nipple and around the woman's back for a snug, overall fit. It is important that the bustier be made as adjustable as possible, since the woman generally would lose a considerable amount of weight in the months after the birth of her baby, as well as the changing size of the breasts throughout a single day.

In yet another embodiment, a back panel and a center panel will be removably attached to the two side portions to allow the woman to adjust the fit of the pumping/nursing bra. In a further embodiment, the front center panel and the straps, as well as the back panel, can be eliminated.

In still a further embodiment, a cover panel would be provided for covering the front of the side panels, allowing the bustier to be worn all day long.

Additional advantages and features of the present invention will be apparent from the following drawings and detailed description of the present invention.

DETAILED DESCRIPTION OF THE PRESENT INVENTION

Figure 1:
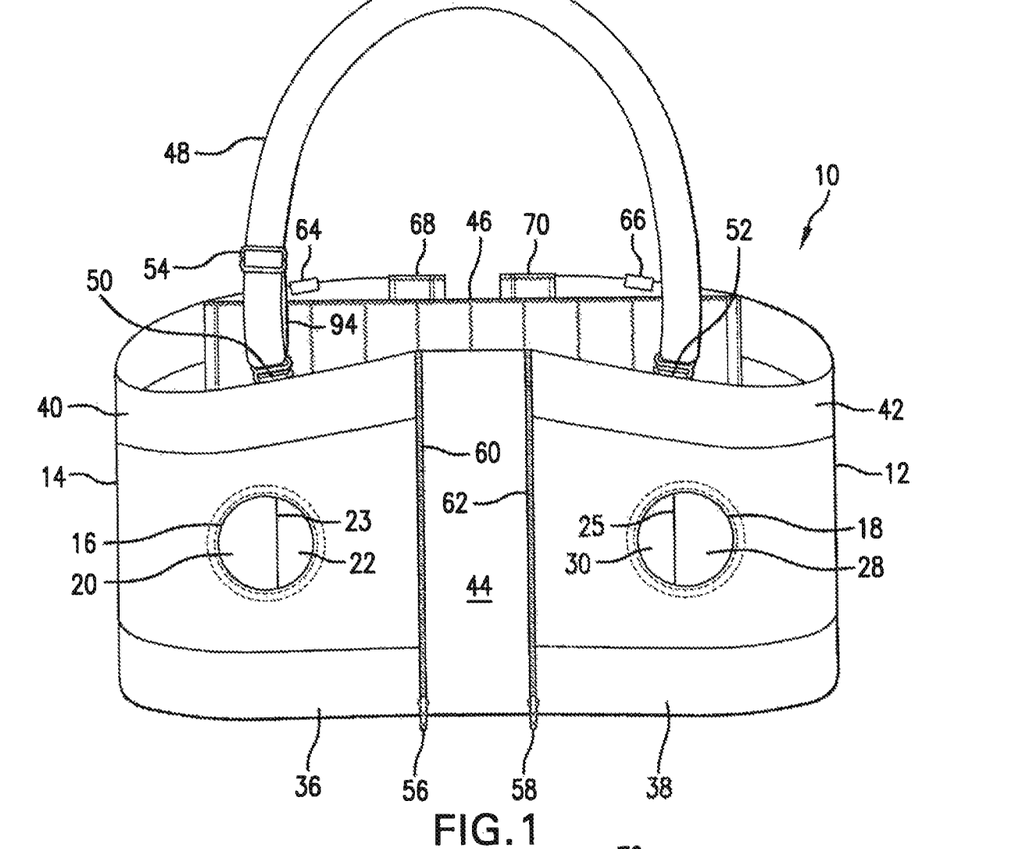
FIG. 1 is a perspective view of the bustier according to the present invention.
Figure 5:
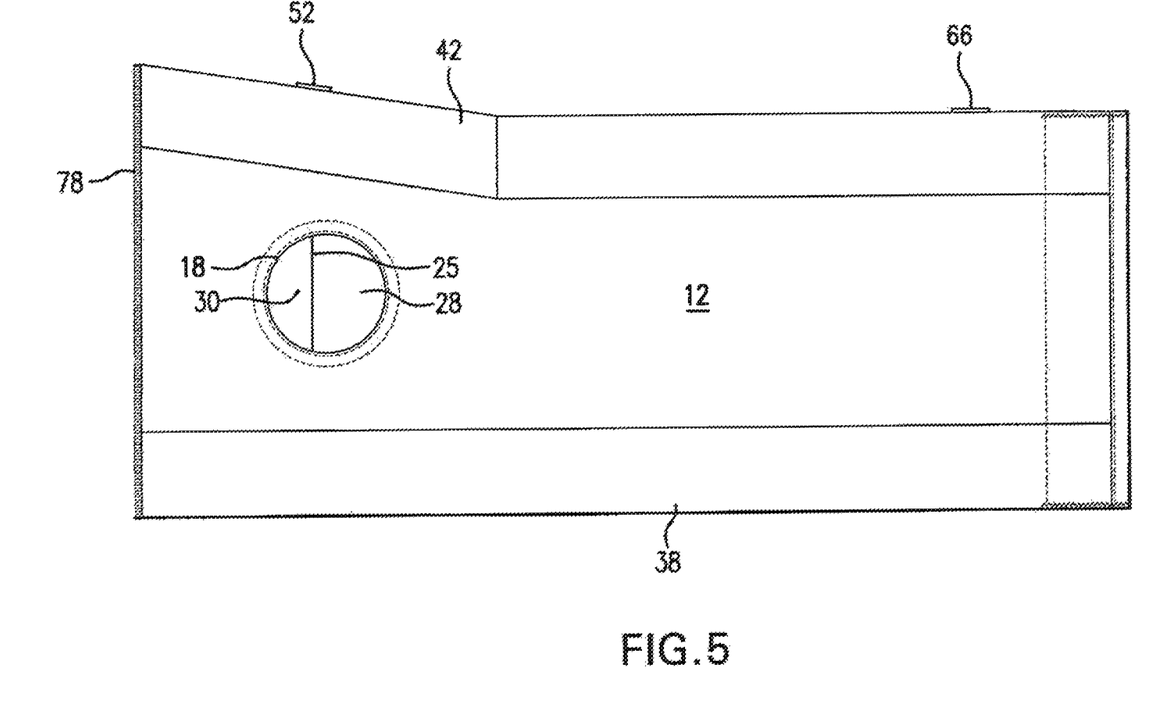
FIG. 5 is a front view of the left panel of the present invention.
Figure 6:
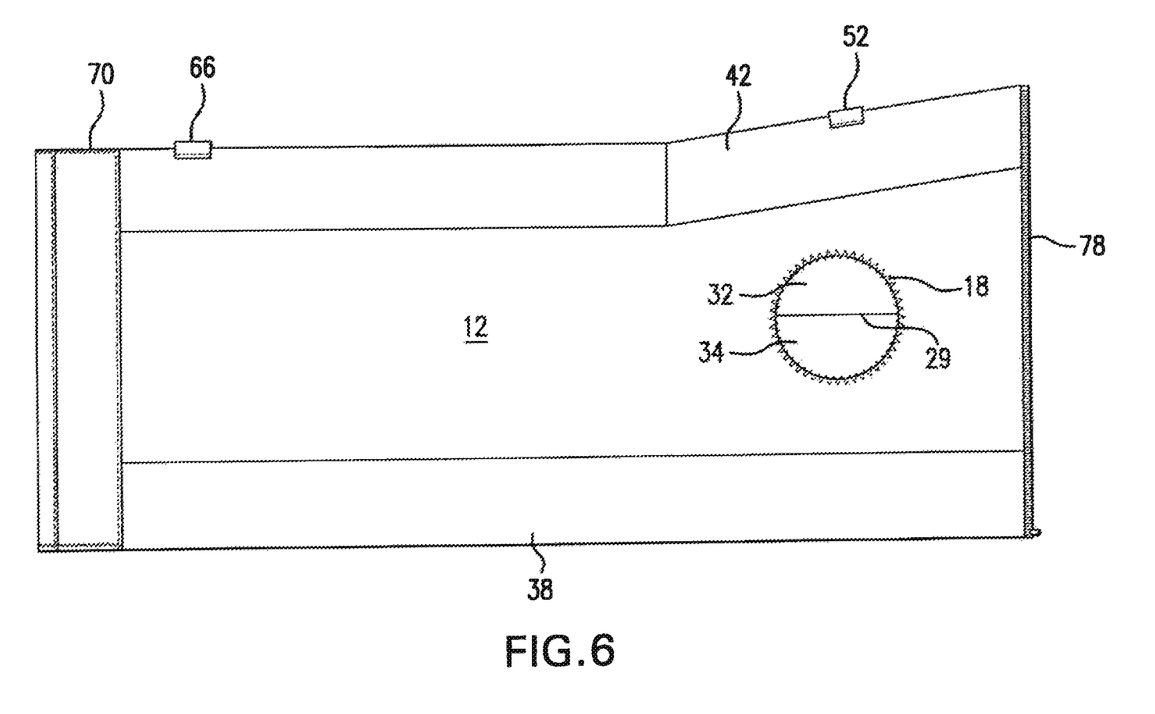
FIG. 6 is a rear view of the left panel of the present invention.

The present invention is illustrated in the drawings where like elements are assigned the same reference numerals. As shown in FIG. 1, the present invention 10 is provided with a left planar panel 12 and a right planar panel 14. The left panel 12 is constructed from a stretchable fabric portion extending for the entire length of the panel 12. A top elastic portion 42, as well as a bottom elastic portion 38, extend along the periphery of the panel 12, with both elastic portions 38, 42 running for the entire length of the left panel 12. The left panel 12 is also provided with an opening 18 through which a standard breast shield or flange would be provided against the woman's breasts. One side of the left panel 12 is provided with one-half of the teeth 78 of a standard zipper, as shown in FIG. 5. The rear side of the left panel is provided with a hook and loop fastener (e.g., VELCRO®) portion 70 running the entire width of the left front panel 12, as shown in FIG. 6, the purpose of which will be explained hereinbelow. Additionally, the opening 18 can be surrounded by a circle of elastic, not shown in the drawings.

Figure 3:
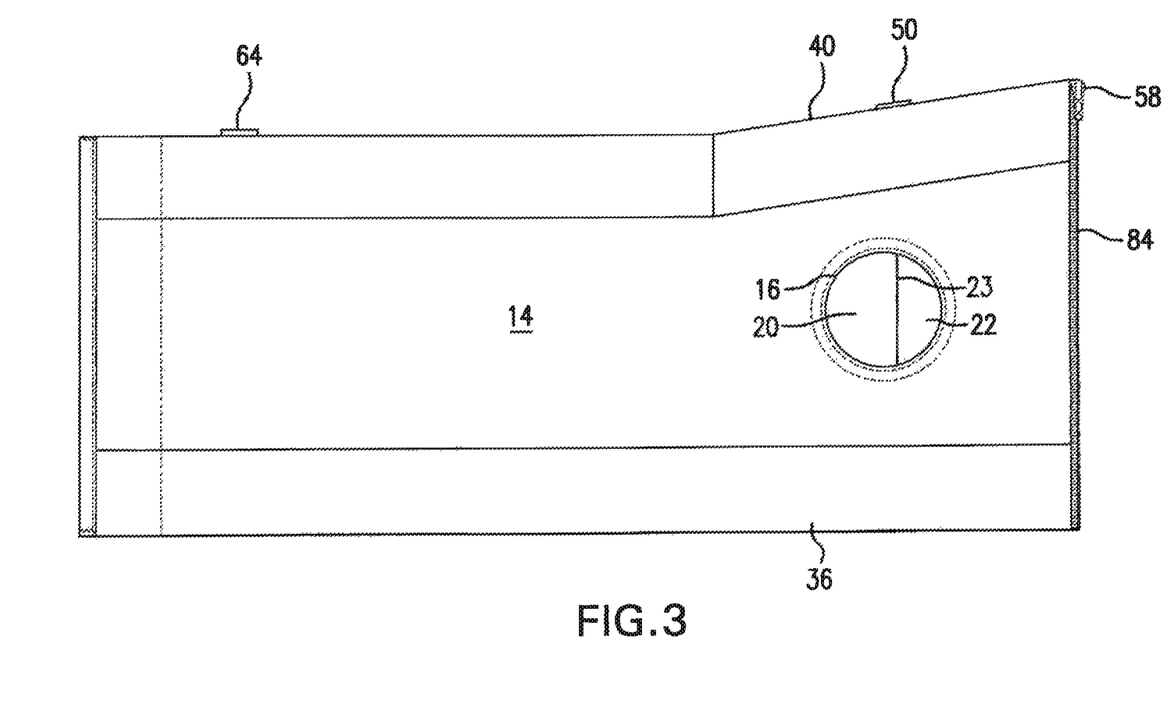
FIG. 3 is a front view of the right panel of the present invention.
Figure 4:
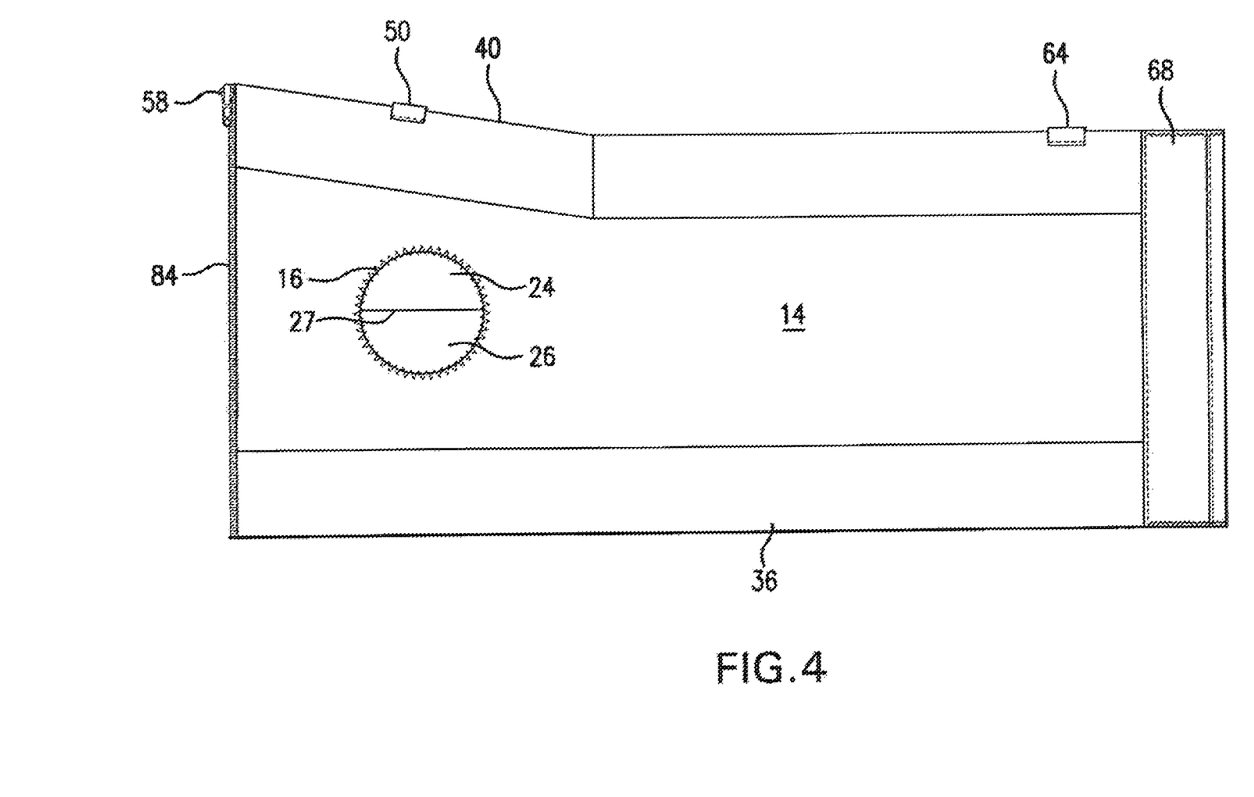
FIG. 4 is a rear view of the right front panel of the present invention.

The right panel 14 is illustrated with respect to FIGS. 1, 3 and 4. Similar to the left panel 12, the right panel 14 is provided with a central portion constructed from a stretchable fabric. This fabric is bounded on the top by an elastic portion 40 and on the bottom by an elastic portion 36. Both elastic portions 36, 40 run the entire length of the right panel 14. An opening 16 is provided corresponding to the woman's breast. The opening 16 can be surrounded by a circular elastic portion (not shown in the drawings). One side of the right panel 14 is provided by a hook and loop fastener (e.g., VELCRO®) portion 68 running the entire width of the end of the panel 14. The opposite end of the right panel 14 contains one-half of the teeth 84 of a standard zipper as well as zipper pull 58 as shown in FIGS. 3 and 4.

The present invention, as shown in FIG. 1, includes an adjustable strap 48, which attaches to both the left panel 12 and the right panel 14. The adjustable strap is provided with hooks 50 and 52 attached to the elastic portion 40 of right panel 14 and the elastic portion 42 of left panel 12, respectively. An adjustable slide 54 is provided for adjusting the length of the strap 48. Movement of the slide 54 would increase or decrease the length of a loop 94, thereby effectively changing the length of the adjustable strap 48, allowing the pumping bra to comfortably fit differently proportioned women.

Figure 7:
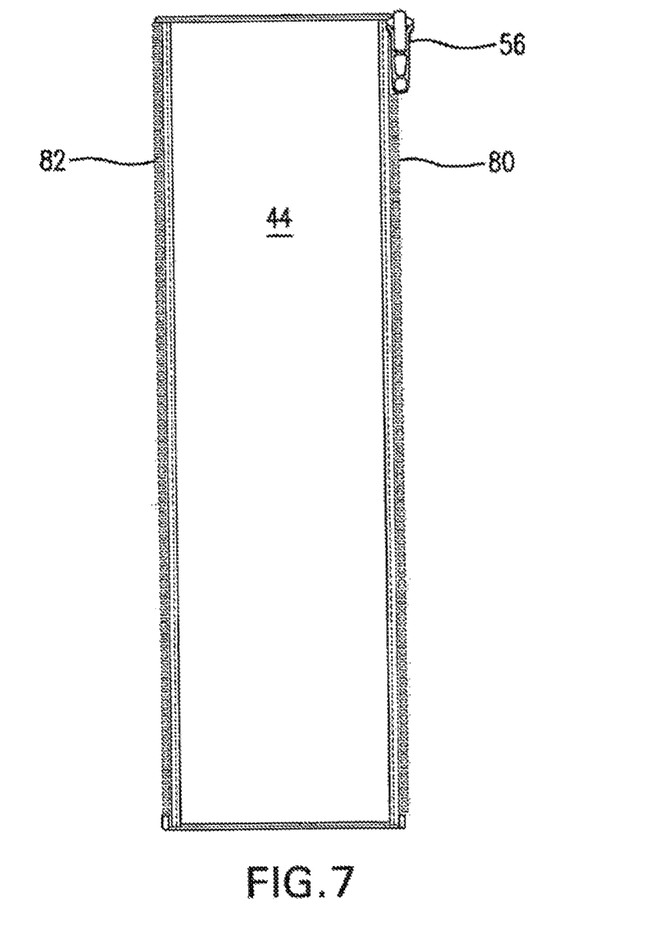
FIG. 7 is a view of the center panel of the present invention.

The embodiment in FIGS. 1, 8, 9, 14, 15 and 20 is designed for the use of a single strap 48 to be worn in a halter style. In one embodiment, each of the left and right panels 12, 14, are attached in the front to a center panel 44. This center panel 44 is constructed from a non-stretchable material, without any elastic portions. As illustrated in FIG. 7, the center panel 44 is provided with two strings of teeth 80 and 82 running the length of the center panel 44, which are used to affix the center panel 44 to the left panel 12 and the right panel 14.

As shown in FIG. 7, the center planar panel 44 is provided with a zipper pull 56 traveling along teeth 80 of the center panel and teeth 78 of the left panel to attach the center panel 44 to the left panel 12, as well as to remove the center panel 44 from the right panel 14, as shown in FIGS. 5 and 6. Similarly, a zipper pull 58 would travel along the teeth 84 provided on one end of the right panel 14, as well as travel along teeth 82 to attach the center panel 44 to the right panel 14 and to remove the center panel 44 from the right panel 14, as shown in FIGS. 3 and 4. It is noted that while zipper pull 58 is shown attached to the right panel 14, it could instead be attached to the left panel 12. What is important is that one of the panels 12 or 14 would be provided with a single zipper pull which is used to attach the center panel 44 to both the left and right panels 12, 14, as shown by the fully attached zipper 60 and 62 shown in FIG. 1. It is noted that in both of these situations, the center panel 44 would only have one zipper pull attached thereto. Furthermore, it is recognized that the center panel 44 can be manufactured in various widths to accommodate different sizes.

As shown in FIGS. 1, 3, 4, 5 and 6, the opening 16 of the right panel 14 and opening 18 of the left panel 12 are covered when not attached to the breast pumps. The opening 16 is covered by four circular pieces of material 20, 22, 24 and 26, as shown in FIGS. 1, 3 and 4. Two circular pieces 20, 22 are attached to the front of the right panel 14, and the additional circular pieces 28, 30 are attached to the front of the left panel 12. These attachments can be accomplished by stitching. These two pairs of circular pieces would then completely cover each respective opening. The size and surface area of circular piece 20 is greater than that of circular piece 22. These pieces would meet at a chord 23. Similarly, the size and surface area of the circular piece 28 is greater than that of circular piece 30 which would meet at a chord 25. It is noted that the chords 23 and 25 are vertically situated. Each of the smaller circular pieces 22 and 30 are situated closer to the center panel than the larger pieces 20 and 28. Alternatively, it is noted that each of the circular pieces of material 20, 22, 24 and 20 could each be semicircular.

Two semicircular pieces of equal size and surface area 24 and 26 are attached to the rear of the right panel 14, covering the opening 16 as shown in FIG. 4. The attachments can be accomplished by stitching. These semicircular pieces meet at a horizontally extending chord 27.

Two semicircular pieces of equal size and surface area 32 and 34 are stitched to the rear of the left panel 12, covering the opening 18 as shown in FIG. 6. These semicircular pieces meet at a horizontally extending chord 29. Although the figures show the fact that chords 23 and 25 are vertical and chords 27 and 29 are horizontal, the orientation of the chords associated with the front circular pieces and the back circular pieces could change. However, it is noted that for efficient operation of the present invention, the front and back chords should be offset 180° with respect to one another. Alternatively, each pair of semicircular pieces of material 32 and 34 and/or 24 and 26 need not be semicircular in nature.

Figure 2:
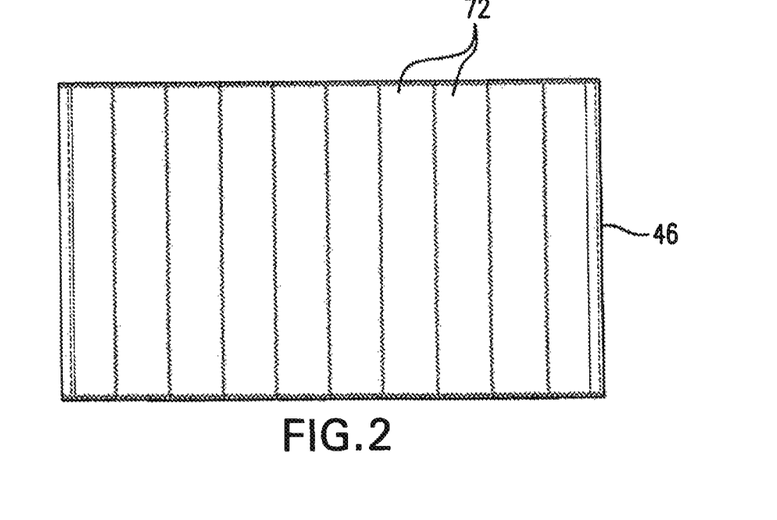
FIG. 2 is a front view of a back panel of the present invention.

As illustrated in FIGS. 1 and 2, the left panel 12, as well as the right panel 14, would be attached in the back to a back planar panel 46 constructed from non-stretchable material. This back panel 46 is provided with stitching approximately every inch for reinforcement and to act as a guide to a woman to help her place hook and loop fastener (e.g., VELCRO®) straps 68 and 70 attached to the end of the right panel 14 and the left panel 12, respectively, in a manner to allow adjustability. This would allow the woman to adjust the total size as her body changes through weight loss or milk supply.

Figure 8:
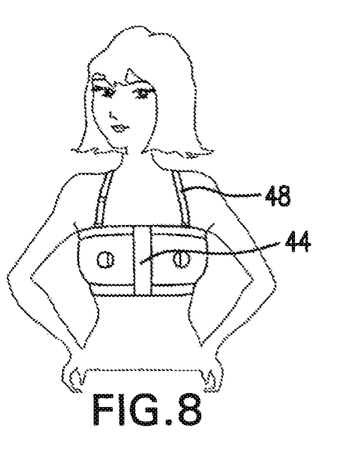
FIGS. 8-20 show front and back views of various embodiments of the present invention worn by a woman.
Figure 9:
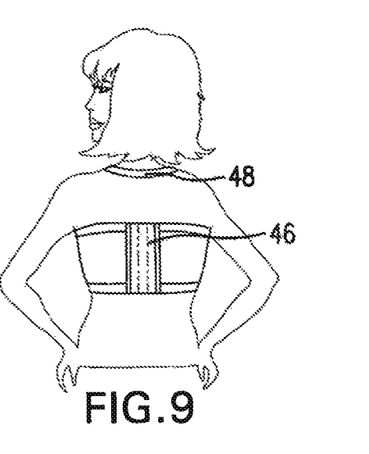
Figure 10:
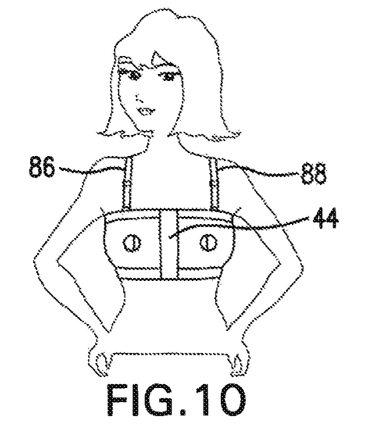
Figure 11:
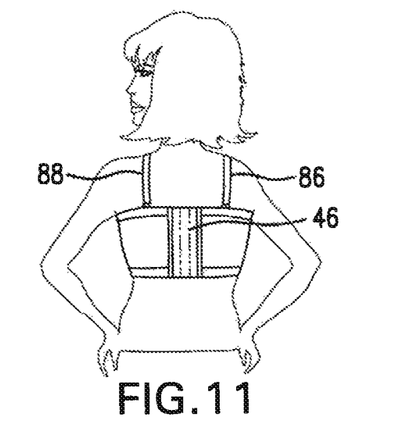

FIGS. 8-13 show embodiments in which both the center panel 44 as well as the back panel 46 are attached to the bustier. FIGS. 8 and 9 show the use of a single attached strap 48 used as a halter. FIGS. 10 and 11 employ two separately adjustable straps 86 and 88 each attaching from the front and back of the same panels. As shown in FIG. 4, a loop 64 is attached to the top surface of the rear portion of the top right elastic portion 40 of the right panel 14 for the purpose of connecting strap 86 between loops 50 and 64. Similarly, a loop 66 is attached to the top left elastic portion 42 near the hook and loop fastener (e.g., VELCRO®) strip 70 allowing attachment of the strap 88 between loops 52 and 66.

Figure 12:
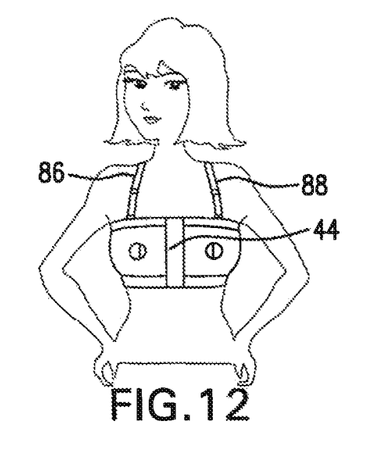
Figure 13:
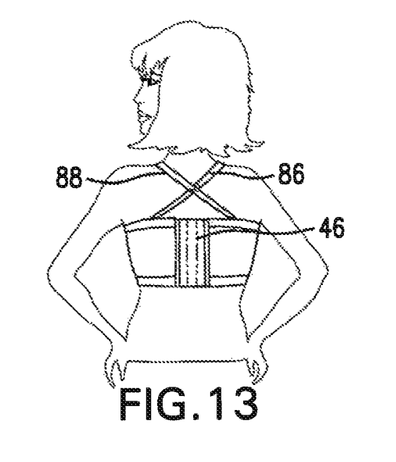

FIGS. 12 and 13 show the use of two adjustable straps 86, 88 which cross in the back of the woman.

Figure 14:
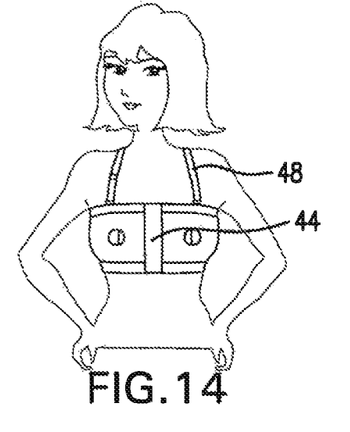
Figure 15:
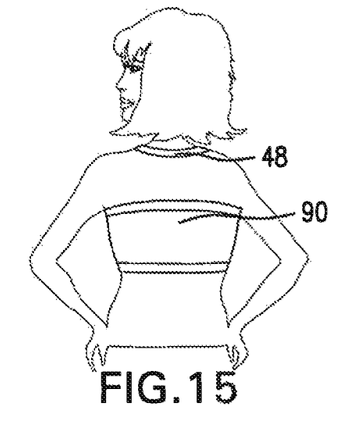

FIGS. 14 and 15 are similar to FIGS. 8 and 9 with the exception that the back panel 46 is not included thereby utilizing only a single panel 90 connected to the center panel 44.

Figure 16:
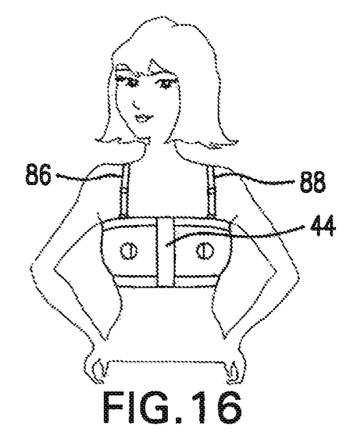
Figure 17:
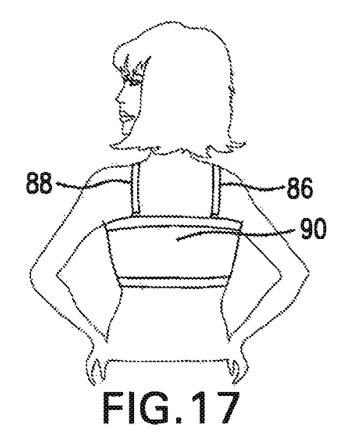
Figure 18:
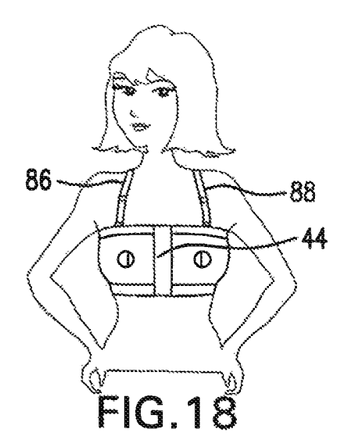
Figure 19:
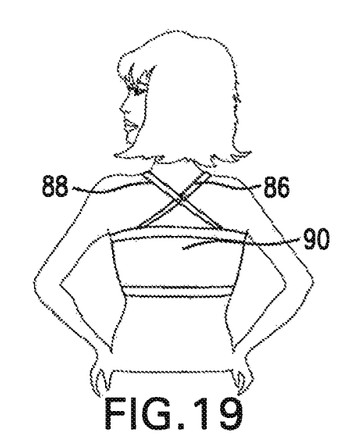

FIGS. 16 and 17 are similar to FIGS. 10 and 11 and FIGS. 18 and 19 are similar to FIGS. 12 and 13 in that the center panel 40 would be utilized in conjunction with only the single panel 90. In the embodiments shown in FIGS. 8-19, it is possible that the center panel 44 need not be utilized. Therefore, in the embodiments shown in FIGS. 8-13, only the back panel 46 would be provided in conjunction with the left panel 12 and the right panel 14. In the embodiments shown with respect to FIGS. 14-20, if the center panel 40 were to be eliminated, the bustier of the present invention would consist of only a single panel 90 completely encircling the woman's chest. In this embodiment, the back panel can also be eliminated.

Figure 20:
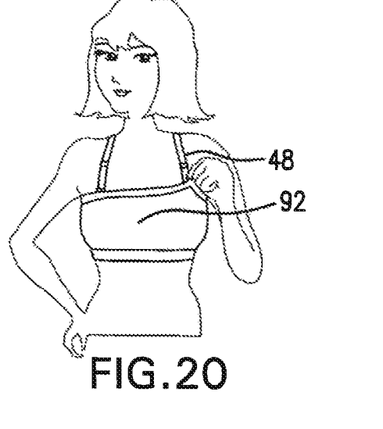

FIG. 20 shows an embodiment in which an additional piece of material 92 would cover the front of the bustier, thereby allowing the woman to wear the present invention as a brassiere. In this embodiment, a hook and loop fastener (e.g., VELCRO®) or any other type of attachment means would be utilized to attach the material 92 to the top periphery as well as the bottom periphery of the front of the bustier.

The bustier of the present invention when used with the center panel 44 would create a fit adjustable to the woman's body. The two zippers of the center panel 44 to the left and right panels 12, 14 would allow the woman to move the breast shield closer together or farther apart by a certain distance, thereby creating a perfect fit. Although the present embodiment utilizes a center panel having a width of two inches, this dimension could be changed. Alternatively, several center panels having larger or smaller widths could be provided to the woman as needed. When not in use as a pumping/nursing bra, by simply slipping nursing pads between each of the openings 16-18, a woman could comfortably and confidently wear the bustier throughout the day as a bra, particularly utilizing the embodiment shown in FIG. 20.

Based upon the changing size of a woman's breast during the day, the plurality of hook and loop fastener (e.g., VELCRO®) attachments 72 constituting the back panel 46 could be used to adjust the fit. The present invention envisions the back panel 46 having a width of ten inches. However, as was true with respect to the width of the center panel 44, the width of the back panel 46 could also change.

In use, the woman would first determine her rib cage band size and then place the hook and loop fastener (e.g., VELCRO®) strip 72 appropriately with respect to the hook and loop fastener (e.g., VELCRO®) strip 68 of the right panel 14 and 70 of the left panel 12. Based upon the woman's size, either the left and right panels would be attached together, through the use of the zipper, or the center panel 44, using the zippers, would be attached to the left and right panels. At this point, a woman would insert each breast shield/flange into the appropriate openings 16 and 18. The woman would then attach a breast pump through one of the openings 16 or 18 by uncovering the four circular pieces associated with each of the openings.

Figure 21:
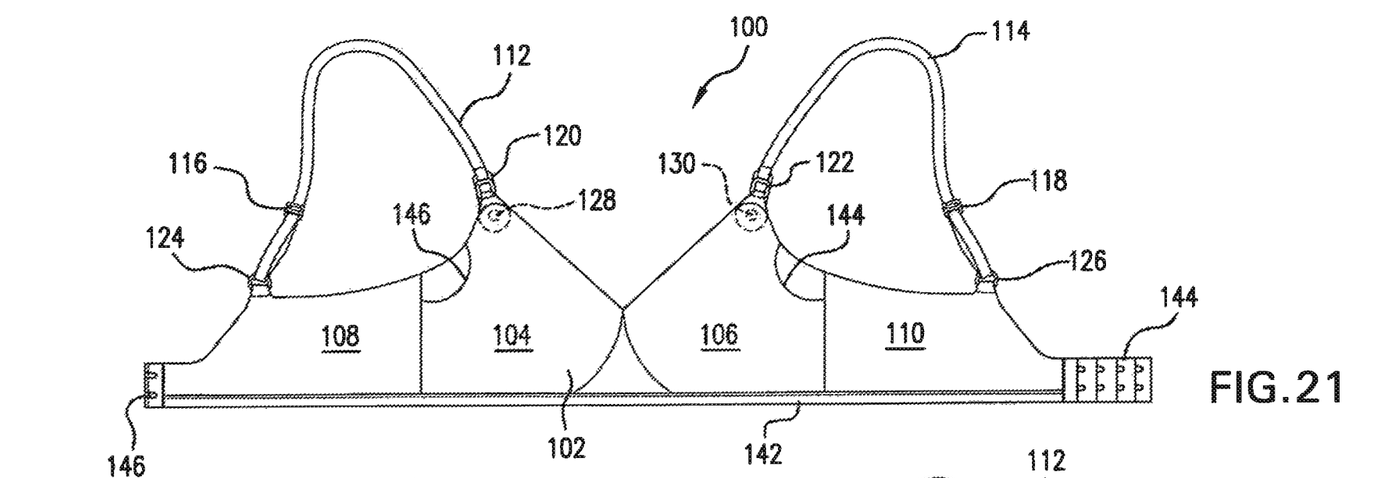
FIG. 21 is a front view of the bustier including a cover panel.

FIGS. 21-24 illustrate in more detail the embodiment described with respect to FIG. 20 in which an additional piece of material would be provided in front of the bustier, allowing a woman to wear the nursing/pumping bra all through the day. The designs shown in FIGS. 21-24 would include the side panels now designated as 136, 138 which were previously described in the present patent application. These side panels 136, 138 would each include openings allowing the woman to nurse or pump her breasts. These openings would be covered by the four circular pieces of material as shown in FIGS. 1, 3 and 4. The embodiments 100 shown in FIGS. 21 and 101 shown in FIG. 23 would not include the center panel 44 or the back panel 46 illustrated in FIG. 1.

Figure 23:
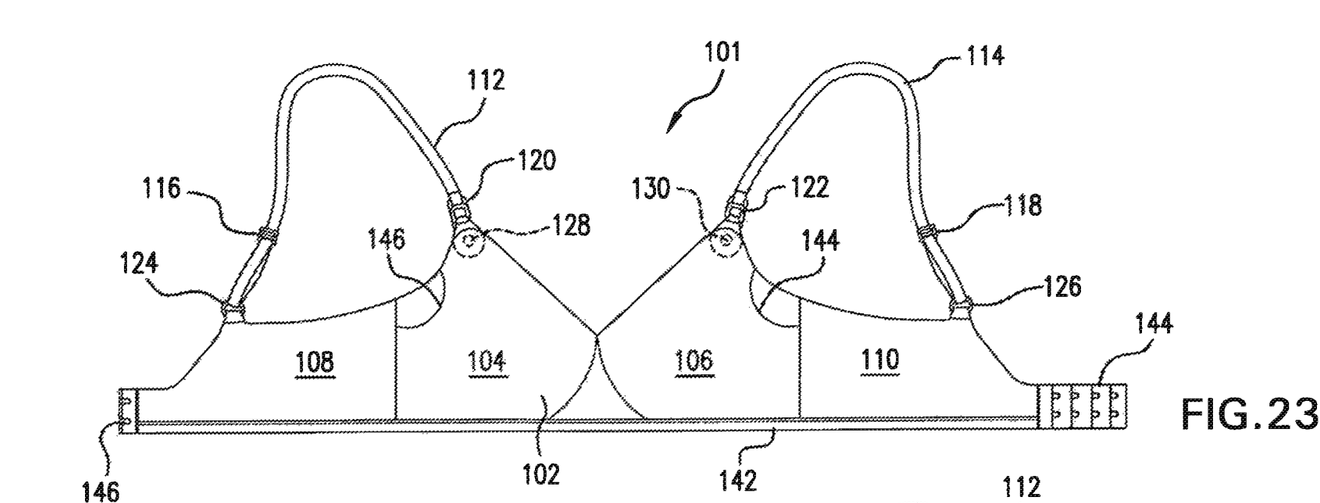
FIG. 23 is a front view of the bustier including a cover panel.

As shown in FIGS. 21 and 23, a cover panel 102 would be applied to the front of what was designated as the side panels 12, 14 shown in FIG. 1. The cover panel 102 includes a first portion 104 adapted to be provided over a side panel 136 which is provided with a breast covering 152 as described with respect to FIG. 1. Similarly, a second portion 106 of the cover panel 102 is to be attached to the side panel 138 provided with circular covering 154 and has been previously described. As shown in FIGS. 21 and 23, a first side section 108 is adjacent to and contiguous with the portion 104 of the cover panel 102. Similarly, a second side section 110 is adjacent to and contiguous with the section 106.

A first shoulder strap 112 is designed to be attached to side section 108 as well as the first portion 104 and the side panel 136 by hook members 124, 120, respectively. An adjustable slide 116 is provided on the shoulder strap 112 to allow the strap 112 to be adjustable for differently sized women. Similarly, a second shoulder strap 114 is attached to the second portion 106, and the side panel 138, as well as to side section 110 through the use of hooks 122, 126, respectively. It is noted that other types of devices for attaching the shoulder strap to the nursing/pumping bra can also be utilized.

A base band member 142 is provided at the bottom of the nursing/pumping bra and bottom portions of the side sections 108, 110 as well as first and second portions 104, 106, and are fixedly attached thereto by stitching or other means of attachment. Ordinary hook and eye attachments 144, 146 are connected to the bottom band portion 142 as well as the side sections 110, 108, respectively to allow the nursing/pumping bra to be secured around the woman's torso.

The interior surface of first portion 104 is provided with a snap 128 cooperating with a rounded aperture provided on the front of side panel 136. Similarly, a snap 130 is provided on the interior surface of the second portion 106 cooperating with a rounded aperture 134 provided on the front of side panel 138. Although a snap connection has been illustrated in FIGS. 21-24, it is noted that any type of detachable connection between portions 104, 136 and 106, 138 can be employed. The purpose of the snap 128 is to detachably affix the top of the first portion 104 from the top of the side panel 136. Similarly, the purpose of the snap 130 is to detachably affix the top of the second portion 106 from the top of the side panel 138. This would allow coverings 152, 154 from being opened, allowing a woman to breast feed or express her milk.

Figure 22:
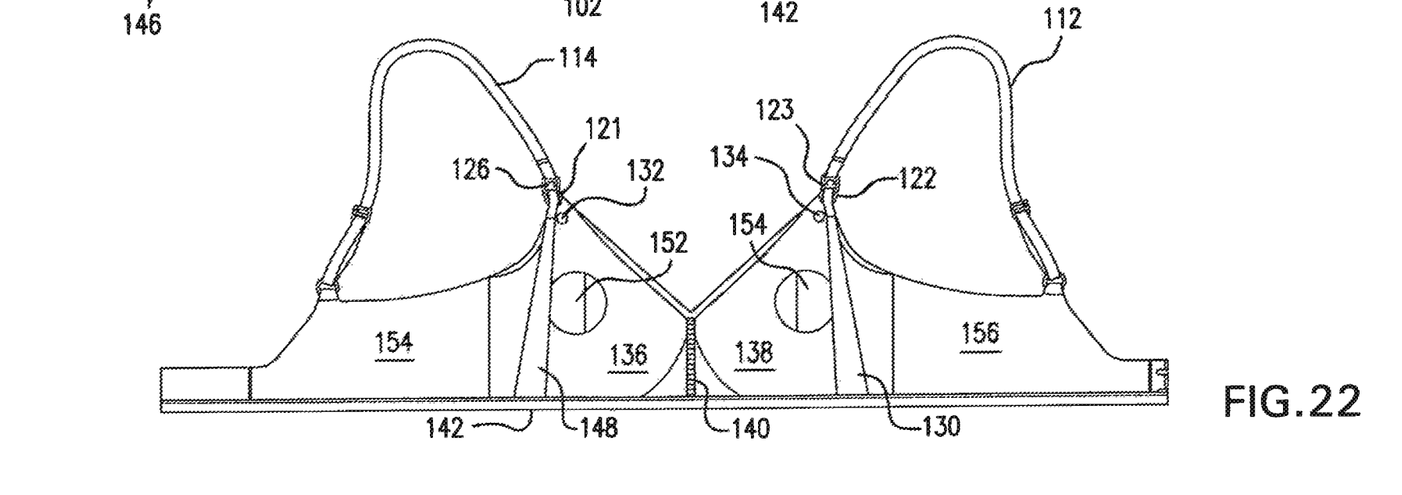
FIG. 22 is a back view of the bustier shown in FIG. 21 having three side panels zipped together.
Figure 24:
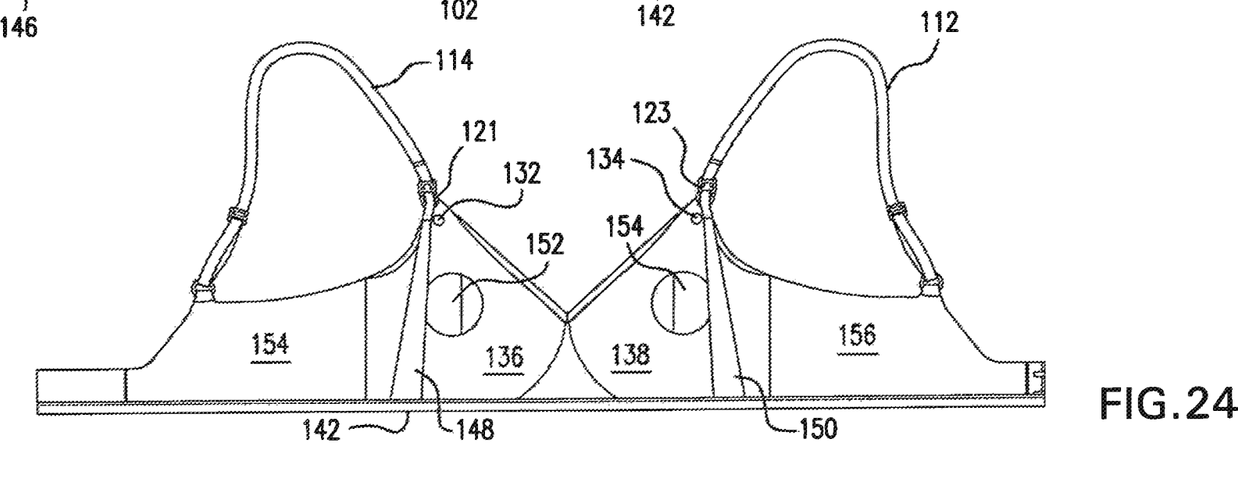
FIG. 24 is a back view of the bustier shown in FIG. 23 having the side panels directly connected to one another.

FIGS. 21 and 23 illustrate the use of side slits 144, 146 used with respect to portions 106, 104, respectively. These slits are shown to be circular in nature. However, any type of slit can be utilized which would allow padding (not shown) to be inserted into the slit. The padding is applied to the front of side panels 136, 138 if needed, to provide a smooth appearance. As shown in FIGS. 22 and 24, side sections 154 and 156 are contiguous with the side panels 136, 138, respectively, corresponding with side sections 108 and 110 shown in FIGS. 21 and 23.

FIGS. 22 and 24 include a first triangularly shaped strap 148 extending between hook 120 and the base band 142. Similarly, a triangularly shaped strap 150 extends between hook 122 and the base band 142. The straps 148, 150 are fixedly attached to the hooks 120, 122 and the base band 142, such as by stitching or any other type of connection. A loop 121 constructed, for example, from a plastic material, connects the top portion of side panel 136 to hook 120. Similarly, a loop 123 constructed, for example, from a plastic material, connects the top portion of side panel 138 to hook 123. Although the straps 148, 150 are triangular in shape, these straps could be rectangular or any other type of configuration. The purpose of the straps 148, 150 is to give support to the bustier when the side panels 136, 138 are detached from the hooks 120, 122 allowing the side panels 136, 138 to hang downwardly and giving access to the breasts directly.

It is noted that the inner layer shown in FIG. 22 is provided with a movable closure, such as a zipper 140 between portions 136, 138. The use of the zipper is not shown in FIG. 24. The cover panel 102 can be made of any fabric, such as cotton, polyester or the like. The pumping/nursing bra can be manufactured in various sizes, such as extra small, small, medium, large, extra large and extra extra large.

Reasonable variations and modifications, which will become apparent to those skilled in the art, can be made in the present invention without departing from the spirit and scope thereof. For example, the non-stretchable fabric portions of the right panel 14, left panel 12, and the center panel 44 could also be constructed from material including up to 3% spandex or any other stretchable material.

What is claimed is:

1. A garment, comprising:
    a panel configured to be disposed over at least a portion of a breast of a wearer of the garment and configured to transition between a first configuration and a second configuration, the panel including a first portion and a second portion collectively defining an opening, the panel configured to receive a portion of a breast pump through the opening such that the breast pump is supported by the panel;
    a band coupled to a bottom edge of the panel;
    a shoulder strap having an attachment mechanism disposed on an end portion of the shoulder strap, the panel being releasably coupled to the attachment mechanism in the first configuration and decoupled from the attachment mechanism in the second configuration; and
    a support strap disposed on an inner side of the panel and having a first end portion coupled to the attachment mechanism and a second end portion coupled to the band when the panel is in the first configuration and the second configuration, the first end portion having a first width and the second end portion having a second width greater than the first width.

2. The garment of claim 1, wherein the panel is an inner panel, and further comprising a cover panel coupled to the inner panel and movable between a first configuration in which the cover panel covers the opening defined by the first portion and the second portion of the inner panel, and a second configuration in which the opening defined by the first portion and the second portion of the inner panel is accessible.

3. The garment of claim 1, wherein the support strap is fixedly coupled to the band.

4. The garment of claim 1, wherein the panel is an inner panel, and further comprising a cover panel coupled to the inner panel, a top portion of the cover panel configured to be coupled to a top portion of the inner panel via a releasable connection mechanism.

5. The garment of claim 1, further comprising:
    a first connector coupled to the shoulder strap and the support strap; and
    a second connector coupled to the panel, the second connector configured to be coupled to the first connector to couple a top portion of the inner panel to the shoulder strap.

6. The garment of claim 5, wherein the first connector includes a hook and the second connector includes a loop configured to be releasably engaged with the hook.

7. A garment, comprising:
    a breast panel configured to be disposed over at least a portion of a breast of a user of the garment, the breast panel including a first portion and a second portion collectively defining an opening, the breast panel configured to receive a portion of a breast pump through the opening such that the breast pump is supported by the breast panel, a shoulder strap having an attachment mechanism disposed on an end portion of the shoulder strap, the breast panel being releasably couplable to the attachment mechanism; and a support strap disposed on an inner side of the breast panel and having a first end portion fixedly coupled to the attachment mechanism and a second end portion fixedly coupled to the bottom edge of the breast panel.

8. The garment of claim 7, further comprising a cover panel coupled to the breast panel and movable between a first configuration in which the cover panel covers the opening defined by the first portion and the second portion of the breast panel, and a second configuration in which the opening defined by the first portion and the second portion of the breast panel is accessible.

9. The garment of claim 7, wherein the first end portion of the support strap has a first width and the second end portion of the support strap has a second width greater than the first width.

10. The garment of claim 8, further comprising:
a first connector attached to the breast panel; and
a second connector attached to the cover panel, the second connector configured to releasably couple at least a portion of the cover panel to the breast panel such that when the first connector is engaged with the second connector the cover panel is in a first configuration in which the cover panel covers the opening and when the first connector is disengaged from the second connector the cover panel can be moved to a second configuration in which the opening is accessible.

11. The garment of claim 10, wherein the first connector is attached to an outer surface of the breast panel and the second connector is attached to an inner surface of the cover panel.

12. The garment of claim 8, further comprising a band coupled to a bottom edge of the breast panel, the cover panel being fixedly attached to the band.

13. A garment, comprising:
a panel configured to be disposed over at least a portion of a breast of a wearer of the garment and configured to transition between a first configuration and a second configuration, the panel including a first portion and a second portion collectively defining an opening, the panel configured to receive a portion of a breast pump through the opening such that the breast pump is supported by the panel;

a band coupled to a bottom edge of the panel;

a shoulder strap having an attachment mechanism disposed on an end portion of the shoulder strap, the panel being releasably coupled to the attachment mechanism in the first configuration and decoupled from the attachment mechanism in the second configuration; and a support strap disposed on an inner side of the panel and having a first end portion fixedly coupled to the attachment mechanism and a second end portion fixedly coupled to the band in both the first configuration and the second configuration of the panel.

14. The garment of claim 13, wherein the panel is an inner panel, and further comprising a cover panel coupled to the inner panel and movable between a first configuration in which the cover panel covers the opening defined by the first portion and the second portion of the inner panel, and a second configuration in which the opening defined by the first portion and the second portion of the inner panel is accessible.

15. The garment of claim 13, wherein the panel is an inner panel, and further comprising a cover panel coupled to the inner panel, a top portion of the cover panel configured to be coupled to a top portion of the inner panel via a releasable connection mechanism.

16. The garment of claim 15, wherein the cover panel is fixedly attached to the band.

17. The garment of claim 13, further comprising:
a first connector coupled to the shoulder strap and the support strap; and
a second connector coupled to the panel, the second connector configured to be coupled to the first connector to couple a top portion of the inner panel to the shoulder strap.

18. The garment of claim 17, wherein the first connector includes a hook and the second connector includes a loop configured to be releasably engaged with the hook.

* * * * *